(12) United States Patent
Wang et al.

(10) Patent No.: US 12,121,895 B2
(45) Date of Patent: Oct. 22, 2024

(54) FULLY AUTOMATED BIOCHIP WORKSTATION AND DETECTION METHOD USING SAME

(71) Applicant: ACADEMY OF MILITARY MEDICAL SCIENCES, Beijing (CN)

(72) Inventors: Shengqi Wang, Beijing (CN); Rui Xiao, Beijing (CN); Zhen Rong, Beijing (CN)

(73) Assignee: ACADEMY OF MILITARY MEDICAL SCIENCES, Beijing (CN)

( * ) Notice: Subject to any disclaimer, the term of this patent is extended or adjusted under 35 U.S.C. 154(b) by 798 days.

(21) Appl. No.: 17/278,243

(22) PCT Filed: Dec. 28, 2018

(86) PCT No.: PCT/CN2018/124571
§ 371 (c)(1),
(2) Date: Mar. 19, 2021

(87) PCT Pub. No.: WO2020/056998
PCT Pub. Date: Mar. 26, 2020

(65) Prior Publication Data
US 2022/0072538 A1    Mar. 10, 2022

(30) Foreign Application Priority Data
Sep. 21, 2018 (CN) .......................... 201811106959.8

(51) Int. Cl.
*B01L 3/00* (2006.01)
*B01L 7/00* (2006.01)
(Continued)

(52) U.S. Cl.
CPC ..... *B01L 3/502715* (2013.01); *B01L 3/50273* (2013.01); *B01L 3/502738* (2013.01);
(Continued)

(58) Field of Classification Search
None
See application file for complete search history.

(56) References Cited

U.S. PATENT DOCUMENTS

| 7,988,933 B2 * | 8/2011 | Vijay ............... G01N 35/00732 422/403 |
| 2004/0033590 A1 | 2/2004 | Su |
| 2016/0186236 A1 | 6/2016 | Kim |

FOREIGN PATENT DOCUMENTS

| CN | 1321890 A | 11/2001 |
| CN | 1683562 A | 10/2005 |

(Continued)

OTHER PUBLICATIONS

PCT Application No. PCT/CN2018/124571, International Search Report mailed May 27, 2019, 2 pp.
(Continued)

*Primary Examiner* — Jyoti Nagpaul
(74) *Attorney, Agent, or Firm* — BKRIP LLC (57) ABSTRACT

Biochip detection apparatus includes a cavity for carrying a test tube vial, the test tube vial being used for accommodating a sample to be detected and a biochip, the cavity having a temperature control function; a liquid storage device for storing liquid; a pumping device for pumping the liquid in the liquid storage device to the test tube vial, the pumping device being in fluid communication with a separation needle for injecting a mixed liquid into the test tube vial; an imaging device for monitoring the chip state in the test tube vial; and a data processing device configured to acquire hybridization results on the basis of information about a biochip state acquired by the imaging device.

19 Claims, 5 Drawing Sheets

Specification includes a Sequence Listing.

(51) Int. Cl.
*G01N 35/10* (2006.01)
*G01N 33/569* (2006.01)

(52) U.S. Cl.
CPC ............... *B01L 7/00* (2013.01); *G01N 35/10* (2013.01); *B01L 2300/0819* (2013.01); *B01L 2300/1805* (2013.01); *B01L 2300/1894* (2013.01); *B01L 2400/0478* (2013.01); *B01L 2400/0666* (2013.01); *G01N 33/56983* (2013.01)

(56) References Cited

FOREIGN PATENT DOCUMENTS

| | | |
|---|---|---|
| CN | 201096779 | 8/2008 |
| CN | 101334402 A1 | 12/2008 |
| CN | 102533525 A1 | 7/2012 |
| CN | 103966082 A | 8/2014 |
| CN | 103966320 A | 8/2014 |
| CN | 104946510 A | 9/2015 |
| CN | 105385589 A | 3/2016 |
| CN | 205347422 U | 6/2016 |
| CN | 106168626 A | 11/2016 |
| CN | 108642159 A | 10/2018 |
| CN | 109055203 A | 12/2018 |
| CN | 209039485 | 6/2019 |
| CN | 110564607 A | 12/2019 |
| JP | 2013236613 A | 11/2013 |
| JP | 2015213465 A | 12/2015 |

OTHER PUBLICATIONS

PCT Application No. PCT/CN2018/124571, Written Opinion mailed May 27, 2019, 5 pp.

Liu, Quanjun et al., Detection and analysis system for hybridization images of lab-in-a-tube microarray, Chinese Science Bulletin, 2005, and vol. 50 and pp. 2896-2900.

Liu, Quanjun et al., Microarray-in-a-Tube for Detection of Multiple Viruses, Clinical Chemistry, 2007, vol. 53, pp. 188-194.

* cited by examiner

SEQUENCE LISTING

<160> NUMBER OF SEQ ID NOS: 12

<210> SEQ ID NO 1

```
<211> LENGTH: 20
<212> TYPE: DNA
<213> ORGANISM: Artificial Sequence
<220> FEATURE:
<223> OTHER INFORMATION: HRSV-F

<400> SEQUENCE: 1
ttaaccagca aagtgttaga                                                  20

<210> SEQ ID NO 2
<211> LENGTH: 21
<212> TYPE: DNA
<213> ORGANISM: Artificial Sequence
<220> FEATURE:
<223> OTHER INFORMATION: HRSV-R

<400> SEQUENCE: 2
tttgttatag gcatatcatt g                                                21

<210> SEQ ID NO 3
<211> LENGTH: 30
<212> TYPE: DNA
<213> ORGANISM: Artificial Sequence
<220> FEATURE:
<223> OTHER INFORMATION: RSVP-A1

<400> SEQUENCE: 3
ccaacaaaag aacaacagac tactagagat                                       30

<210> SEQ ID NO 4
<211> LENGTH: 25
<212> TYPE: DNA
<213> ORGANISM: Artificial Sequence
<220> FEATURE:
<223> OTHER INFORMATION: AQF1

<400> SEQUENCE: 4
gccccagcgg tctaacatgc acatc                                            25

<210> SEQ ID NO 5
<211> LENGTH: 23
<212> TYPE: DNA
<213> ORGANISM: Artificial Sequence
<220> FEATURE:
<223> OTHER INFORMATION: AQR1

<400> SEQUENCE: 5
gccacggtgg gttttcttta ctt                                              23

<210> SEQ ID NO 6
<211> LENGTH: 24
<212> TYPE: DNA
<213> ORGANISM: Artificial Sequence
<220> FEATURE:
<223> OTHER INFORMATION: AdvP1

<400> SEQUENCE: 6
tgcaccagac ccgggctcag gtac                                             24

<210> SEQ ID NO 7
<211> LENGTH: 20
<212> TYPE: DNA
<213> ORGANISM: Artificial Sequence
<220> FEATURE:
<223> OTHER INFORMATION: Influenza As

<400> SEQUENCE: 7
```

```
aaagcgaatt tcagtgtgat                                              20

<210> SEQ ID NO 8
<211> LENGTH: 19
<212> TYPE: DNA
<213> ORGANISM: Artificial Sequence
<220> FEATURE:
<223> OTHER INFORMATION: Influenza A as

<400> SEQUENCE: 8
gaaggcaatg gtgagattt                                               19

<210> SEQ ID NO 9
<211> LENGTH: 20
<212> TYPE: DNA
<213> ORGANISM: Artificial Sequence
<220> FEATURE:
<223> OTHER INFORMATION: INFA

<400> SEQUENCE: 9
agggctttca ccgaagaggg                                              20

<210> SEQ ID NO 10
<211> LENGTH: 20
<212> TYPE: DNA
<213> ORGANISM: Artificial Sequence
<220> FEATURE:
<223> OTHER INFORMATION: Influenza Bs

<400> SEQUENCE: 10
gtccatcaag ctccagtttt                                              20

<210> SEQ ID NO 11
<211> LENGTH: 20
<212> TYPE: DNA
<213> ORGANISM: Artificial Sequence
<220> FEATURE:
<223> OTHER INFORMATION: Influenza B as

<400> SEQUENCE: 11
tcttcttaca gcttgcttgc                                              20

<210> SEQ ID NO 12
<211> LENGTH: 23
<212> TYPE: DNA
<213> ORGANISM: Artificial Sequence
<220> FEATURE:
<223> OTHER INFORMATION: INFB

<400> SEQUENCE: 12
aacgaagtag gtggagacgg agg                                          23
```

FULLY AUTOMATED BIOCHIP WORKSTATION AND DETECTION METHOD USING SAME

The present disclosure claims the priority to the Chinese patent application with the filing No. 201811106959.8 filed with the Chinese Patent Office on Sep. 21, 2018, and entitled "Fully Automatic Biochip Workstation and Detection Method Using Same", the contents of which are incorporated herein by reference in entirety.

TECHNICAL FIELD

The present disclosure relates to the field of chip hybridization apparatuses, in particular, to a fully automated biochip workstation and a detection method using the same.

BACKGROUND ART

Biochip hybridization refers to reaction of protein, DNA or RNA sample separated from a biological sample with a biochip, to obtain sequence information of the sample from a probe array immobilized on the biochip. As the fluorescence background of the slide itself is very low, detection and analysis may be performed on the biochip using a fluorescence labeling method, which meanwhile has the advantages such as being fast and precise. Moreover, a plurality of fluorescein may also be used for labeling so as to analyze a plurality of biological samples one time.

Currently, some apparatuses related to biochip hybridization have been disclosed, but there is no disclosure about an integrated instrument for nucleic acid amplification and hybridization.

In view of this, the present disclosure is specifically proposed.

SUMMARY

Objectives of the present disclosure include providing a biochip detection apparatus, which realizes integration of biochip reaction with detection result output, improves the processing efficiency of samples, and saves the manpower, with a stable and reliable result.

Objectives of the present disclosure further include providing a method for detecting a biochip, wherein the whole detection process is automatically operated, with high detection efficiency, and stable and reliable detection result.

In order to achieve at least one of the above objectives or other possible objectives of the present disclosure, the following technical solution is adopted:

A biochip detection apparatus, including a cavity configured to carry a test tube vial, wherein the test tube vial is configured to accommodate a sample to be detected and a biochip, and the cavity has a temperature control function;
  a liquid storage device configured to store a liquid;
  a pumping device configured to pump the liquid in the liquid storage device to the test tube vial, wherein the pumping device is in fluid communication with a liquid separating needle for injecting a mixed liquid into the test tube vial;
  an imaging device configured to monitor a chip state in the test tube vial; and
  a data processing device configured to acquire a hybridization result on the basis of information of the biochip state acquired by the imaging device.

Optionally, there are a plurality of test tube vials, the cavity is divided into a plurality of spaces for carrying different test tube vials, and a top surface of each space is provided with a receptacle to be inserted by a corresponding test tube vial.

Optionally, one side of the cavity has a hollowed portion, and the imaging device captures information of the biochip in the test tube vial body through the hollowed portion; a vial body of the test tube vial is a flat structure, and/or the vial body is made of a transparent material.

Optionally, the cavity is provided to be adapted to the vial body structure of the test tube vial; and/or a top portion of the cavity is provided with a groove for receiving a cap of the test tube vial.

Optionally, the biochip detection apparatus further includes a bracket for supporting the liquid separating needle, wherein the bracket is provided above the cavity and is movable up and down; and the bracket is provided with a liquid separating pinhole for the liquid separating needle to pass therethrough.

Optionally, the cap of the test tube vial is provided corresponding to the liquid separating needle; and optionally, the liquid separating needle is inserted in the cap corresponding to the test tube vial, and is inserted into the test tube vial.

Optionally, a liquid discharging needle for discharging the liquid in the test tube vial is further provided, and the liquid discharging needle is in fluid communication with a liquid discharging device.

Optionally, the bracket is configured to support the liquid discharging needle, and optionally, the bracket is provided with a liquid discharging pinhole for the liquid discharging needle to pass therethrough.

Optionally, the liquid discharging needle is provided adjacent to the liquid separating needle, and the cap of the test tube vial is correspondingly provided with one liquid separating needle and one liquid discharging needle.

Optionally, two ends of the cavity are each provided with a guide rail along a vertical direction, and two ends of the bracket are slidably connected to corresponding guide rails through guide blocks, respectively.

Optionally, the cavity is provided with a heating and cooling sheet at the bottom, to realize temperature control of the cavity through cold and heat conduction.

Optionally, the heating and cooling sheet is a thermoelectric cooling sheet, and the thermoelectric cooling sheet realizes conversion of its cooling and heating functions by means of a control electrode.

Optionally, a heat dissipation device, such as at least one of a cooling fin and a fan, is further provided below the heating and cooling sheet.

Optionally, there are a plurality of test tube vials, and the cavity is divided into spaces for carrying different test tube vials.

Optionally, the liquid storage device includes a plurality of liquid storage bottles, and the plurality of liquid storage bottles control mixing and outflow of different solutions through a liquid separating valve.

Optionally, the liquid separating valve includes any one or a combination of an eight-way valve, a four-way valve, and a three-way valve.

Optionally, a cover plate for fastening the test tube vial is further provided between the bracket and the cavity; and optionally, the cover plate is provided with holes corresponding to the liquid separating needle and the liquid discharging needle.

Optionally, a platform is further included, and the cavity, the liquid storage device, the pumping device, the bracket, and the imaging device are all mounted on the platform.

Optionally, the cavity is mounted on one side of the platform, the bracket is mounted above the cavity, a mounting plate is vertically fixed on the other side of the platform close to the cavity, the liquid storage bottle of the liquid storage device is fixed on a side surface of the mounting plate facing away from the cavity, a pumping device is located between the cavity and the mounting plate, and the imaging device is mounted on one side of the cavity in parallel.

Optionally, the imaging device may be movably disposed.

Optionally, the hollowed side of the cavity is provided with a rail along a direction parallel to the cavity, and the imaging device is slidably connected to the rail through a sliding block.

The present disclosure further provides a method for detecting a biochip, which is performed using the above biochip detection apparatus, and the steps are as follows:

placing a biochip, a sample to be detected, and a primer into the test tube vial fixed in the cavity;

controlling inflow and outflow of the liquid in the test tube vial and the temperature, so as to realize amplification of the sample to be detected and hybridization of an amplification product with the biochip; and performing corresponding treatment using different detection manners, acquiring, by an imaging device, information of the biochip having undergone the hybridization, and processing a hybridization result by a data processing device to obtain a result.

Optionally, the liquid in the liquid storage device is pumped by the pumping device into the test tube vial through the liquid separating needle, and the liquid in the test tube vial is pumped out to the liquid discharging device through the liquid discharging needle.

Optionally, the amplification of the sample to be detected and the hybridization of the amplification product with the biochip are performed simultaneously, and a buffer solution used is a PCR amplification buffer solution.

A temperature control procedure may be correspondingly adjusted according to different detected objects and different detection methods, for example, it may be a typical PCR reaction program, may also be a double temperature PCR, such as a double temperature PCR of 94° C. and 55° C., and may also be constant temperature amplification such as LAMP/RPA.

Optionally, the temperature control procedure is: denaturation, annealing, and extension, for multiple cycles.

Optionally, the temperature control procedure is: 94±1° C. for 10±2 s, 55±1° C. for 20±2 s, and 72±2° C. for 20±2 s, 35-40 cycles.

Optionally, the detection manner includes a chemiluminescence method, a fluorescence method, and a visualization method.

In practical operations, different detection manners may be adopted for detection, or the same detection manner may be adopted.

If different detection manners are adopted, a reagent involved in corresponding detection manner is added each time, and an image is displayed with a corresponding method, so as to obtain the hybridization result of different detected objects of the corresponding sample upon repeated detection.

For example, the same kind of detection method may select to use different markers according to the objects to be detected, so as to obtain the hybridization result of different detected objects of corresponding samples through treatment under different conditions. In the chemiluminescence method, for example, a horseradish enzyme-labeled avidin solution is added, after the hybridization is completed, a luminescent substrate is added, and a high-sensitivity CCD imaging element (Model JAI CM-030-GE) moves on the guide rail to be directly in front of each chip to collect a chemiluminescence biochip image.

In the fluorescence method, for example, an avidin-labeled quantum dot SA-QDs625 solution is added, after the hybridization is completed, the ultraviolet light source is used for excitation, followed by filtration, and the high-sensitivity CCD imaging element moves on the guide rail to be directly in front of each chip to collect a quantum dot fluorescence biochip image.

In the visualization method, for example, an avidin-labeled quantum dot SA-QDs625 solution is added, after the hybridization is completed, a silver-stained substrate solution is added, followed by cleaning, a white LED light source is turned on, and the CCD imaging element moves on the guide rail to be directly in front of each chip, to collect a visualization biochip image.

In addition to the above quantum dots and biotin, the substance displaying a signal involved in the present disclosure further may include fluorescent substance, digoxin-labeled probe, radioactive isotope, radioactive contrast agent, paramagnetic ion fluorescent microsphere, electron dense substance, chemiluminescent marker, ultrasonic contrast agent, photosensitizer, colloidal gold or enzyme.

In the above, the fluorescent substance includes any one of Alexa 350, Alexa 405, Alexa 430, Alexa 488, Alexa 555, Alexa 647, AMCA, aminoacridine, BODIPY 630/650, BODIPY 650/665, BODIPY-FL, BODIPY-R6G, BODIPY-TMR, BODIPY-TRX, 5-carboxy-4', 5'-dichloro-2', 7'-dimethoxyfluorescein, 5-carboxy-2', 4', 5', 7'-tetrachlorofluorescein, 5-carboxyfluorescein, 5-carboxyrhodamine, 6-carboxyrhodamine, 6-carboxytetramethyl rhodamine, Cascade Blue, Cy2, Cy3, Cy5, Cy7, 6-FAM, dansyl chloride, fluorescein, HEX, 6-JOE, NBD(7-nitrobenzo-2-oxa-1, 3-diazole), Oregon Green 488, Oregon Green 500, Oregon Green 514, Pacific Blue, phthalic acid, terephthalic acid, isophthalic acid, cresol fast violet, cresol blue violet, brilliant cresol blue, p-aminobenzoic acid, erythrosine, phthalocyanine, azomethine, cyanine, xanthine, succinyl fluorescein, rare earth metal cryptate, tri-dipyridyldiamine europium, europium cryptate or chelate, diamine, bianthocyanin, La Jolla blue dye, allophycocyanin, allococcyanin B, phycocyanin C, phycocyanin R, thiamine, phycoerythrin and phycocyanin, phycoerythrin R, REG, rhodamine green, rhodamine isothiocyanate, rhodamine red, ROX, TAMRA, TET, TRIT (tetramethylrhodamine isothiol), tetramethylrhodamine, and Texas red.

The radioactive isotope includes any one of $^{110}In$, $^{111}In$, $^{177}Lu$, $^{18}F$, $^{52}Fe$, $^{62}Cu$, $^{64}Cu$, $^{67}Cu$, $^{67}Ga$, $^{68}Ga$, $^{86}Y$, $^{90}Y$, $^{89}Zr$, $^{94}mTc$, $^{94}Tc$, $^{99}mTc$, $^{120}I$, $^{123}I$, $^{124}I$, $^{125}I$, $^{131}I$, $^{154-158}Gd$, $^{32}P$, $^{11}C$, $^{13}N$, $^{15}O$, $^{186}Re$, $^{188}Re$, $^{51}Mn$, $^{52}mMn$, $^{55}Co$, $^{72}As$, $^{75}Br$, $^{76}Br$, $^{82}mRb$, and $^{83}Sr$.

The enzyme includes any one of horseradish peroxidase, alkaline phosphatase, and glucose oxidase.

The fluorescent microspheres are: polystyrene fluorescent microsphere, internally wrapped with rare earth fluorescent ion europium.

Compared with the prior art, the beneficial effects of the present disclosure at least include:

(1) The cavity having the temperature control function is provided in the present disclosure, so that the amplification of the sample to be detected and the hybridization of the sample to be detected with the biochip are operated integrally, thus greatly saving the operation steps, and saving the time.

(2) In the present disclosure, the mixing of different liquids is controlled by the liquid separating valve, and the mixed liquid flows in the test tube vial through the liquid separating needle, so as to satisfy the requirement of solutions in different stages, meanwhile, the waste liquid is discharged through the liquid discharging needle, thus realizing full automation of the hybridization process.

(3) The present disclosure is further provided with the imaging device so as to acquire the information of the biochip in the vial, thus realizing automated operation of result acquisition, and saving the manpower.

(4) The biochip detection apparatus provided in the present disclosure realizes the automated operation of the whole process of biochip detection, thus improving the detection efficiency, with a stable and reliable detection result.

BRIEF DESCRIPTION OF DRAWINGS

In order to more clearly illustrate technical solutions in specific embodiments of the present disclosure or the prior art, accompanying drawings which need to be used for description of the specific embodiments or the prior art will be introduced briefly below. Apparently, the accompanying drawings in the description below merely show some embodiments of the present disclosure, and those ordinarily skilled in the art still could obtain other accompanying drawings in light of these accompanying drawings, without using any creative efforts.

REFERENCE SIGNS

1—cavity; 2—liquid storage bottle; 3—pumping device; 4—bracket; 5—imaging device; 6—liquid separating valve; 7—space; 8—receptacle; 9—hollowed portion; 10—groove; 11—liquid separating pinhole; 12—liquid discharging pinhole; 13—guide block; 14—guide rail; 15—platform; 16—mounting plate; 17—PCB board.

DETAILED DESCRIPTION OF EMBODIMENTS

Technical solutions of the present disclosure will be described clearly and completely below in combination with the accompanying drawings and specific embodiments, while a person skilled in the art would understand that the following embodiments described are some but not all embodiments of the present disclosure, and they are merely used for illustrating the present disclosure, but should not be considered as limiting the scope of the present disclosure. All of other embodiments obtained by those ordinarily skilled in the art based on the embodiments in the present disclosure without using creative efforts shall fall within the scope of protection of the present disclosure. If no specific conditions are specified in the embodiments, they are carried out under normal conditions or conditions recommended by manufacturers. If manufacturers of reagents or apparatuses used are not specified, they are conventional products commercially available.

In the description of the present disclosure, it should be indicated that orientation or positional relations indicated by terms "center", "upper", "lower", "left", "right", "vertical", "horizontal", "inner", "outer" and so on are based on orientation or positional relations as shown in the accompanying drawings, merely for facilitating the description of the present disclosure and simplifying the description, rather than indicating or implying that related devices or elements have to be in the specific orientation or configured and operated in a specific orientation, therefore, they should not be construed as limiting the present disclosure. Besides, terms "first", "second", and "third" are merely for descriptive purpose, but should not be construed as indicating or implying importance in the relativity.

In the description of the present disclosure, it should be noted that unless otherwise specified and defined explicitly, terms "mount", "join", "connect" should be construed in a broad sense. For example, it may be fixed connection, detachable connection, or integral connection; it may be mechanical connection, and also may be electrical connection; it may be direct connection, indirect connection via an intermediate medium, or inner communication between two elements. For those ordinarily skilled in the art, specific meanings of the above-mentioned terms in the present disclosure could be understood according to specific circumstances.

Figure 1:
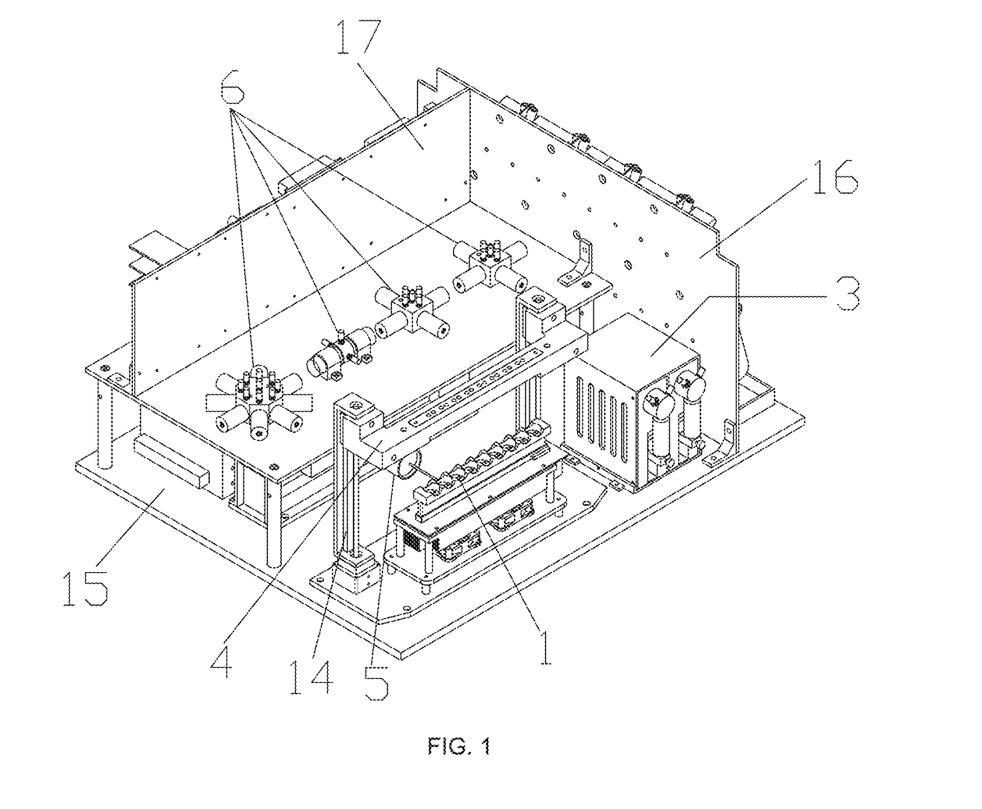
FIG. 1 is a front perspective view of a biochip detection apparatus provided in an embodiment of the present disclosure.
Figure 2:
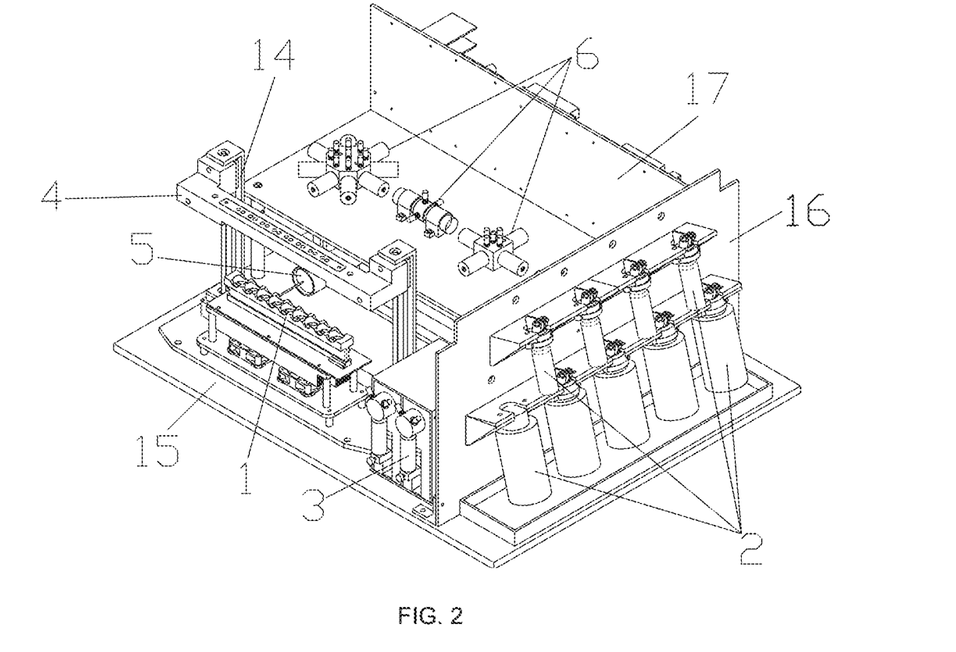
FIG. 2 is a side perspective view of the biochip detection apparatus provided in an embodiment of the present disclosure.
Figure 3:
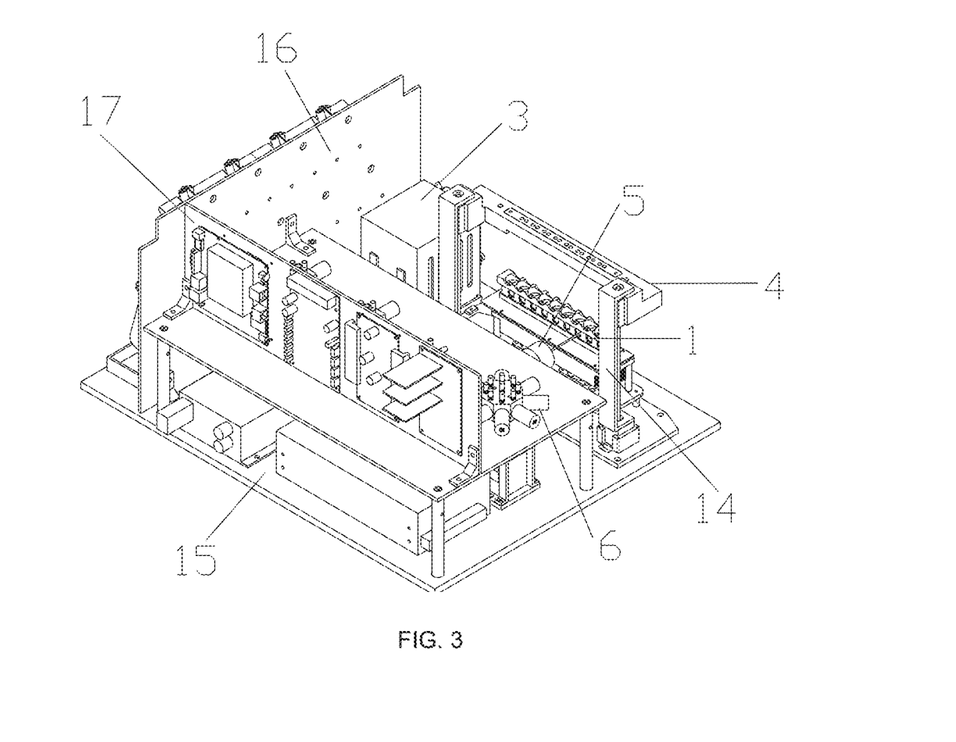
FIG. 3 is a rear perspective view of the biochip detection apparatus provided in an embodiment of the present disclosure.

As shown in FIGS. 1-3, a biochip detection apparatus provided in the present disclosure includes a cavity 1 configured to carry a test tube vial, wherein the test tube vial is used for accommodating a sample to be detected and a biochip, and the cavity 1 has a temperature control function;

a liquid storage device configured to store a liquid;

a pumping device 3 configured to pump the liquid in the liquid storage device to the test tube vial, wherein the pumping device 3 is in fluid communication with a liquid separating needle for injecting a mixed liquid into the test tube vial;

an imaging device 5 configured to monitor a chip state in the test tube vial; and a data processing device, configured to acquire a hybridization result on the basis of information of the biochip state acquired by the imaging device 5.

It should be noted that the existing process of the biochip hybridization and the hybridization result detection is as follows:

preparing a biochip with different probes: different probe buffer solutions are spotted on a substrate with a gene chip sample applicator, and dried for subsequent use;

preparing a PCR product for hybridization: performing PCR amplification on an object to be detected; and performing hybridization on the biochip and the PCR product: the PCR amplification product is denatured (98° C.), immediately subjected to cold bath, and then mixed with a hybridization buffer solution, wherein the mixed liquid is added to a sample application area of the chip, the chip is placed into a hybridization box, and subjected to hybridization in an oven in a light-tight condition; and after being washed in a light-tight condition, the resultant is scanned and analyzed.

For the biochip detection apparatus provided in the present disclosure, the sample to be detected and the biochip are directly added to the test tube vial, the temperature is controlled by the temperature control function of the cavity 1, the pumping device 3 enables corresponding solution in the liquid storage device to flow into the test tube vial or control the liquid in the test tube vial to flow out, the sample to be detected is hybridized with the biochip while being subjected to the PCR amplification, then by adding a corresponding washing liquid, different detection manners are adopted for treatment, the imaging device 5 acquires the information of the biochip having undergone the hybridization, and the result is obtained after the hybridization result is processed by the data processing device.

It should be noted that the biochip in the present disclosure not only includes the gene chip, but also includes a protein chip, that is, the biochip detection apparatus provided in the present disclosure not only can be used for gene detection, but also can be used for protein immunodetection, for example.

The present disclosure realizes the automated operation of the whole process of biochip detection, thus improving the detection efficiency, with a stable and reliable detection result.

Figure 4:
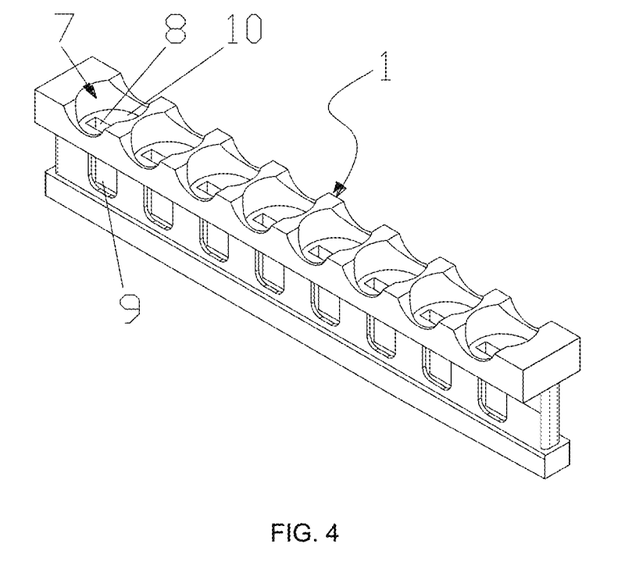
FIG. 4 is a structural schematic view of a cavity in the biochip detection apparatus provided in an embodiment of the present disclosure.

In the present disclosure, the cavity 1 is configured to carry the test tube vial, and the cavity 1 may be completely surrounded by a side wall, and may also be configured as a frame. In order to realize analysis of multiple biological samples one time, there may be a plurality of test tube vials, and referring to what is shown in FIG. 4, the cavity 1 is divided into a plurality of spaces 7 for carrying different test tube vials, a top surface of each space 7 is configured for insertion of a receptacle 8 of a corresponding test tube vial, the cavity 1 is provided with a plurality of independent spaces 7, and each space 7 is configured to place one test tube vial.

In order to facilitate photographing and temperature control, in some embodiments, one side of the cavity 1 has a hollowed portion 9 (FIG. 4), and the imaging device 5 captures the information of the biochip in the vial body through the hollowed portion 9.

Optionally, a camera of the imaging device 5 is provided directly opposite to the part of the hollowed portion 9, so as to facilitate the image capturing.

In some embodiments, the vial body of the test tube vial is a flat structure. As the vial body is used for holding the biochip and the sample to be detected, the biochip is generally a quadrangular sheet, and the sample to be detected is a liquid, the shape of the vial body needs to be set similar to the biochip; furthermore, the volume shape of the vial body is slightly bigger than that of the biochip, the flat structure facilitates easy placement of the biochip, and by providing a plane of the flat structure towards the imaging device 5, the imaging device 5 also conveniently captures information of the biochip.

In some embodiments, the vial body is made of a transparent material, so as to ensure the sharpness of the image in the vial, and facilitate the imaging device 5 in capturing the information of the biochip.

In some embodiments, the cavity 1 is provided to be adapted to the vial body structure, and specifically, the size of each space 7 is set to be adapted to the size of the corresponding test tube vial. As the cavity 1 is temperature-controlled, and the temperature of the test tube vial is generally controlled by the heat conduction of the cavity 1, the cavity 1 is provided to be structurally adapted to the vial body structure, and the stability of the placement of the test tube vial may also be enhanced. Optionally, as an example, with reference to FIG. 4, the vial body is a flat structure, and is configured to carry the test tube vial in a square flat shape, which not only facilitates the heat conduction, but also facilitates stable insertion of the test tube vial into the corresponding space 7. In some embodiments, the top portion of the cavity 1 is provided with a groove 10 for accommodating a cap of the test tube vial, and by providing the groove 10, the cap of the test tube vial is positioned, thus enhancing the stability of the cap, so as to facilitate the control insertion or pull-out of the liquid separating needle or other infusion needles on the cap.

In some embodiments, the biochip detection apparatus further includes a bracket 4 for supporting the liquid separating needle, wherein the bracket 4 is provided above the cavity 1 and is movable up and down.

The liquid separating needle is provided above the test tube vial, and located on the bracket 4, and the liquid separating needle is inserted into or pulled out of the test tube vial through the movement of the bracket 4. As an example, with reference to FIG. 5, the bracket 4 is provided with a liquid separating pinhole 11 for the liquid separating needle to pass therethrough, and the liquid separating needle is inserted into the liquid separating pinhole 11 to realize the function of supporting the liquid separating needle.

In some embodiments, the cap of the test tube vial is provided corresponding to the liquid separating needle, that is, one space 7 carries one test tube vial, and the cap of one test tube vial is correspondingly inserted with one liquid separating needle; and optionally, the liquid separating needle is inserted into the cap of the corresponding test tube vial, and inserted into the test tube vial.

In different stages of the hybridization process, different solutions are required for treatment, and the automated operation of liquid change is realized through the inflow and the discharge of the liquid.

In some embodiments, a liquid discharging needle for discharging the liquid in the test tube vial is further provided, and the liquid discharging needle is in fluid communication with the liquid discharging device. The liquid discharging needle discharges the liquid to the liquid discharging device, such as a waste bottle.

Figure 5:
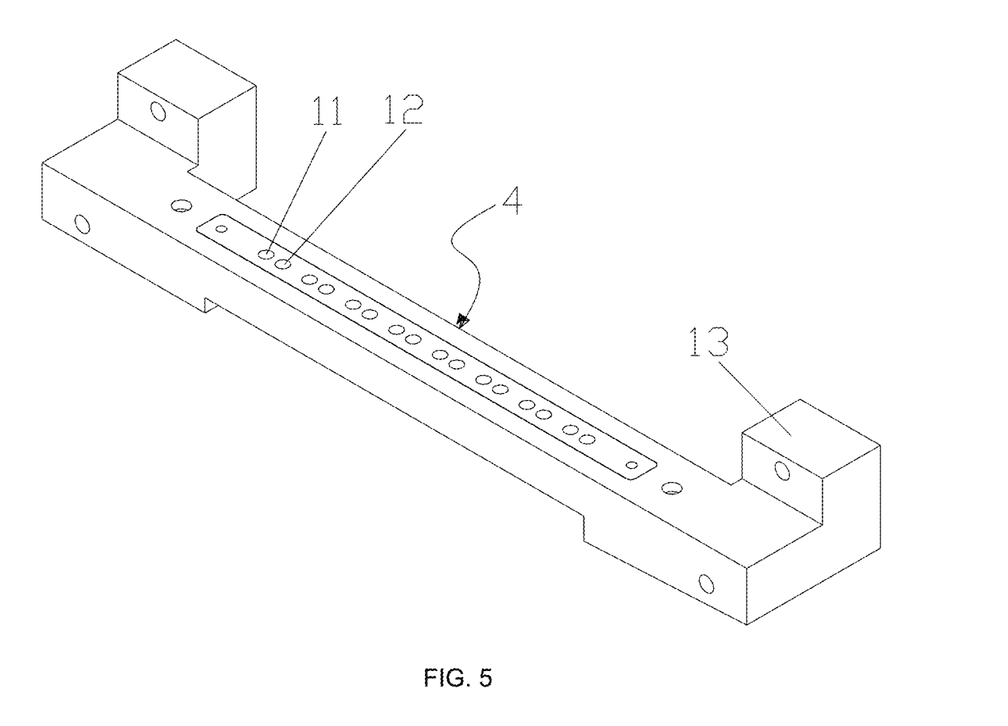
FIG. 5 is a structural schematic view of a bracket in the biochip detection apparatus provided in an embodiment of the present disclosure.

In some embodiments, the bracket 4 is further configured to support the liquid discharging needle, and optionally, with reference to FIG. 5, the bracket is provided with a liquid discharging pinhole 12 for the liquid separating needle to pass therethrough, and the liquid discharging needle is inserted into the liquid discharging pinhole 12 to realize the function of supporting the liquid discharging needle.

In some embodiments, referring to FIG. 5, the liquid discharging pinholes 12 and the liquid separating pinholes 11 are arranged in pairs, the paired liquid discharging pinhole 12 and liquid separating pinhole 11 are arranged adjacent to each other, and correspondingly, the liquid discharging needle and the liquid separating needle are provided adjacent to each other, and the cap of each test tube vial is correspondingly provided with one liquid separating needle and one liquid discharging needle. That is, in each test tube vial, the inflow of the liquid is controlled by the liquid separating needle and the discharge of the liquid is controlled by the liquid discharging needle, thus realizing the automated operation of the liquid change.

In some embodiments, two ends of the cavity 1 are each provided with a guide rail 14 along a vertical direction, and two ends of the bracket 4 are slidably connected to the corresponding guide rails 14 through guide blocks 13, respectively. By controlling the movement of the bracket 4 along the guide rails 14, the up and down movement of the bracket 4 is realized, so that the bracket drives the liquid separating needle and the liquid discharging needle to move up and down, and to be inserted into or pulled out from the cap of the test tube vial.

In some embodiments, the cavity 1 is provided with a heating and cooling sheet at the bottom, to realize temperature control of the cavity 1 by cold and heat conduction.

In some embodiments, the heating and cooling sheet is a thermoelectric cooling sheet, and the thermoelectric cooling sheet realizes the conversion of its cooling and heating functions by means of a control electrode.

In some embodiments, a heat dissipation device is further provided below the heating and cooling sheet, and optionally, the heat dissipation device includes at least one of a cooling fin, a fan and so on.

Temperature control in the test tube vial is realized by the heating device and the heat dissipation device.

In some embodiments, the liquid storage device includes a plurality of liquid storage bottles 2, and the plurality of liquid storage bottles 2 control mixing and outflow of different solutions through a liquid separating valve 6. The liquid storage bottles 2 are in fluid communication with the liquid separating needle, and specifically, the liquid storage bottles 2 are in fluid communication with the pumping device 3, and the pumping device 3 is in fluid communication with the liquid separating needle.

In some embodiments, the liquid separating valve 6 includes any one or a combination of an eight-way valve, a four-way valve, and a three-way valve.

In some embodiments, a cover plate for fastening the test tube vial is further provided between the bracket 4 and the cavity 1, and the cover plate is provided with holes corresponding to the liquid separating needle and the liquid discharging needle.

By providing the cover plate, the test tube vial is placed more fixedly.

In some embodiments, a platform 15 is further included, wherein the cavity 1, the liquid storage device, the pumping device 3, the bracket 4, and the imaging device 5 are all mounted on the platform 15, and all units are grouped together by the platform 15 to form an integral body. In addition, the cover plate is elastically connected to the platform 15.

In some embodiments, the cavity 1 is mounted on one side of the platform 15, the bracket 4 is mounted above the cavity 1, a mounting plate 16 is vertically fixed on the other side of the platform 15 close to the cavity, the liquid storage bottles 2 of the liquid storage device are fixed on a side surface of the mounting plate 16 facing away from the cavity, the pumping device 3 is located between the cavity 1 and the mounting plate 16, and the imaging device 5 is mounted on one side of the cavity 1 in parallel, then vertical arrangement of a plurality of liquid storage bottles 2 is realized through the mounting plate 16. A PCB board 17 is vertically mounted on a side of the platform 15 opposite to the cavity 1, and the liquid separating valve is located between the PCB board 17 and the cavity 1.

In some embodiments, the imaging device 5 is movably provided.

In some embodiments, the side of the cavity 1 having the hollowed portion 9 is provided with a rail along a direction parallel to the cavity 1, and the imaging device 5 is slidably connected to the rail through a sliding block.

In practical operation, the position of the imaging device 5 is controlled according to test tube vials at different positions, so as to acquire the information of the biochips in different test tube vials.

For the biochip detection apparatus provided in the present disclosure, the flow of liquid, the movement of the bracket 4, and so on are completed by a control system, and the control system and a data processing system are provided on a same operation page.

The control system includes a PCB board 17 and the like, for example, a microprocessor chip, a temperature control module, a driving module, a touch liquid crystal screen module, a USB module, a JTAG module, an alarm module and the like are mounted on the PCB board 17, and the microprocessor chip is connected to various modules, respectively, and controls various modules, so as to realize accurate operation of the whole operation.

The present disclosure further provides a method for detecting a biochip, performed using the above biochip detection apparatus, and the steps are as follows:

placing a biochip, a sample to be detected, and a primer into a test tube vial fixed in a cavity 1;

controlling inflow and outflow of the liquid in the test tube vial and the temperature, thereby realizing amplification of the sample to be detected and hybridization of an amplification product with the biochip; and performing corresponding treatment using different detection manners, acquiring, by an imaging device 5, information of the biochip having undergone the hybridization, and processing a hybridization result by a data processing device to obtain a result.

In some embodiments, the liquid in the liquid storage bottle 2 is pumped by the pumping device 3 into the test tube vial through a liquid separating valve 6 and a liquid separating needle, and the liquid in the test tube vial is pumped out to the liquid discharging device through the liquid discharging needle, to realize inflow and outflow of the liquid in the test tube vial.

In some embodiments, by sliding on the rail to be opposite to the hollowed portion 9 of a space 7 where a target test tube vial is located, the imaging device 5 acquires information of the biochip in the test tube vial.

It should be noted that the biochip detection apparatus provided in the present disclosure is not installed with various pipes or the like, and may be used only when corresponding installation is performed.

Specific example is as follows:

Influenza A, influenza B, RSV, and adenovirus of samples were detected, and primers and probes of these several detected objects were designed according to a conventional method, which are specifically as shown in Table 1.

These sequences are also provided in the accompanying sequence listing, titled "sequence_listing," created Jul. 30, 2021, with a size of 2,512 bytes, the disclosure of which is incorporated herein in its entirety by reference.

TABLE 1

Specific Sequences

| Name | Sequence (5'-3') | Target Virus |
|---|---|---|
| HRSV-F | TTAACCAGCAAAGTGTTAGA | respiratory syncytia |
| HRSV-R | Bio-TTTGTTATAGGCATATCATTG | |
| RSVP-A1 | CCAACAAAAGAACAACAGACTACTAGAGAT | |
| AQF1 | GCCCCAGCGGTCTAACATGCACATC | respiratory adenovirus |
| AQR1 | Bio-GCCACGGTGGGTTTTCTTTACTT | |
| AdvP1 | TGCACCAGACCCGGGCTCAGGTAC | |
| Influenza As | AAAGCGAATTTCAGTGTGAT | influenza A |
| Influenza A as | Bio-GAAGGCAATGGTGAGATTT | |
| INFA | AGGGCTTTCACCGAAGAGGG | |
| Influenza Bs | GTCCATCAAGCTCCAGTTTT | influenza B |
| Influenza B as | Bio-TCTTCTTACAGCTTGCTTGC | |
| INFB | AACGAAGTAGGTGGAGACGGAGG | |

Figure 6:
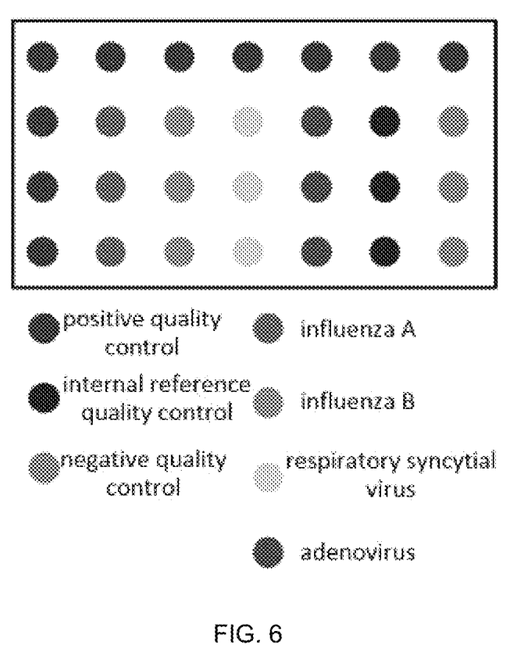
FIG. 6 is a dot array diagram of various samples of the biochip provided in an embodiment of the present disclosure.

The nucleic acid probe sample application: the biochip was a self-produced aldehyde slide, the concentration of probe sample application was 10 UM, and the samples were stored at room temperature in a dry condition, as shown in FIG. 6.

PCR amplification: a nucleic acid sample (object to be detected), a biochip, and a PCR mix reagent (including a primer and a buffer solution) were mixed, and added to the test tube vial of instrument. The cycling parameters of the semiconductor heating and cooling sheet of the instrument are: 94° C. for 10 s, 55° C. for 20 s, 72° C. for 20 s, for 40 cycles, to realize amplification and hybridization simultaneously. The washing liquid was then pumped in through an injection pump and a solenoid valve to clean the chip.

Subsequently, three detection manners, namely, chemiluminescence, quantum dot fluorescence, and visualization were realized using three types of instrument and reagents, respectively.

Figure 7:
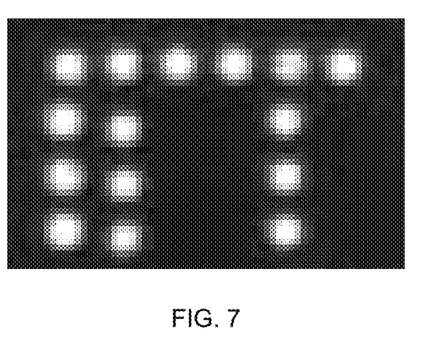
FIG. 7 is a diagram of chemiluminescence detection result of the biochip provided in an embodiment of the present disclosure.

Chemiluminescence method detection: 100 μL of horseradish enzyme-labeled avidin solution was automatically pumped into each reaction bottle, and reacted at 37° C. for 30 min. A PBST washing liquid was pumped in for cleaning. Then 100 μL of chemiluminescence substrate solution (Millipore hypersensitive chemiluminescent substrate solution, liquid A: liquid B=1:1) was pumped in. The high-sensitivity CCD imaging element (Model JAI CM-030-GE) moved to be directly in front of each chip on the guide rail, and collected chemiluminescent biochip images, wherein exposure time of each chip was 10 s, and there were 8 chips in total. Results are as shown in FIG. 7. This image result indicates that this sample is positive for influenza A nucleic acid.

Figure 8:
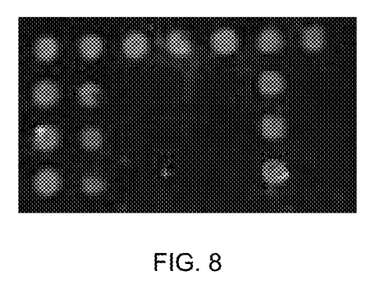
FIG. 8 is a diagram of fluorescence detection result of the biochip provided in an embodiment of the present disclosure.

Fluorescence method detection, 100 μL 25 nM avidin-labeled red quantum dot SA-QDs 625 solution (Wuhan Jiayuan) was automatically pumped into each reaction bottle, and reacted at 37° C. for 30 min. The PBST washing liquid was pumped in for cleaning. 5 W UV LED light source with wavelength of 365 nm was turned on to excite QDs to emit fluorescence, the fluorescence was filtered by a filter (624/40 nm, model Edmund Optical 67-021), the high-sensitivity CCD imaging element moved on the guide rail to be directly in front of each chip to collect a quantum dot fluorescence biochip image, wherein the exposure time of each chip was 10 s, and there were 8 chips in total. Results are as shown in FIG. 8. This image result indicates that this sample is positive for influenza A nucleic acid.

Figure 9:
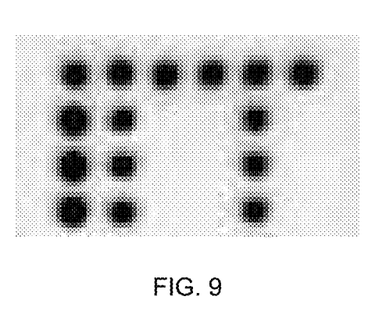
FIG. 9 is a diagram of visualization detection result of the biochip provided in an embodiment of the present disclosure.

Visualization detection: 100 μL 25 nM avidin-labeled red quantum dot SA-QDs 625 solution (Wuhan Jiayuan) was automatically pumped into each reaction bottle, and reacted at 37° C. for 30 min. The PBST washing liquid was pumped in for cleaning. Then 100 μL of silver-stained substrate solution was pumped in, followed by reaction for 5 min, and the resultant was washed with deionized water. A white light LED light source was turned, a CCD imaging element moved on the guide rail to be directly in front of each chip to collect a quantum dot fluorescence biochip image, wherein there were 8 chips in total. Results are as shown in FIG. 9. This image result indicates that this sample is positive for influenza A nucleic acid.

For the biochip detection apparatus provided in the present disclosure, the sample to be detected and the biochip are directly added to the test tube vial, by controlling the temperature and the inflow and outflow of corresponding solutions, the reaction product of the sample PCR amplification is detected with the biochip while the amplification is being performed, then by adding corresponding washing liquid, the chip is photographed to obtain the information, and the final hybridization result may be obtained. It realizes integration of the hybridization process of the gene biochip and output of result, improves the processing efficiency of the sample, and saves the manpower, with a more stable and more reliable result.

Finally, it should be indicated that the various embodiments above are merely used for illustrating the technical solutions of the present disclosure, rather than limiting the present disclosure; while the detailed description is made to the present disclosure with reference to the various preceding embodiments, those ordinarily skilled in the art should understand that they still could modify the technical solutions recited in the various preceding embodiments, or make equivalent substitutions to some or all of the technical features therein; and these modifications or substitutions do not make the essence of the corresponding technical solutions depart from the scope of the technical solutions of the various embodiments of the present disclosure.

INDUSTRIAL APPLICABILITY

The present disclosure provides a biochip detection apparatus and a biochip detection method, which realize integration of biochip reaction with detection result output, and automated operation of the whole detection process, thus improving the processing efficiency of the samples, and saving the manpower, with a stable and reliable result.

What is claimed is:

1. A method for detecting a biochip, wherein the method is performed using a biochip detection apparatus comprising:

a cavity configured to carry a test tube vial, wherein the test tube vial is configured to accommodate a sample to be detected and a biochip, and the cavity has a temperature control function;

a liquid storage device, configured to store a liquid;

a pumping device, configured to pump the liquid in the liquid storage device to the test tube vial, wherein the pumping device is in fluid communication with a liquid separating needle for injecting a mixed liquid into the test tube vial;

an imaging device, configured to monitor a chip state in the test tube vial; and a data processing device, configured to acquire a hybridization result based on information of a state of the biochip acquired by the imaging device, wherein the method has following steps:

placing a biochip, a sample to be detected, and a primer into the test tube vial, wherein the test tube vial is fixed in the cavity;

controlling inflow and outflow of the liquid in the test tube vial and a temperature, so as to realize amplification of the sample to be detected and hybridization of an amplification product with the biochip; and performing corresponding treatment using different detection manners, acquiring, by an imaging device, information of the biochip having undergone hybridization, and processing a hybridization result by a data processing device to obtain a result.

2. The method for detecting a biochip according to claim 1, wherein the liquid in the liquid storage device is pumped by the pumping device into the test tube vial through the liquid separating needle, and the liquid in the test tube vial is pumped out to the liquid discharging device through the liquid discharging needle.

3. The method for detecting a biochip according to claim 1, wherein a plurality of test tube vials are provided, the cavity is divided into a plurality of spaces for carrying different test tube vials, and a top surface of each of the spaces is provided with a receptacle to be inserted by a corresponding test tube vial.

4. The method for detecting a biochip according to claim 1, wherein one side of the cavity has a hollowed portion, and the imaging device captures information of the biochip in a vial body of the test tube vial through the hollowed portion; and the vial body of the test tube vial is a flat structure, and/or the vial body is made of a transparent material.

5. The method for detecting a biochip according to claim 1, wherein the cavity is provided to be adapted to a structure of the vial body of the test tube vial; and/or a top portion of the cavity is provided with a groove for receiving a cap of the test tube vial.

6. The method for detecting a biochip according to claim 1, wherein the biochip detection apparatus further comprises a bracket for supporting the liquid separating needle, wherein the bracket is provided above the cavity and is movable up and down; and the bracket is provided with a liquid separating pinhole for the liquid separating needle to pass therethrough.

7. The method for detecting a biochip according to claim 6, wherein the cap of the test tube vial is provided corresponding to the liquid separating needle.

8. The method for detecting a biochip according to claim 6, wherein the biochip detection apparatus is further provided with a liquid discharging needle for discharging the liquid in the test tube vial, wherein the liquid discharging needle is in fluid communication with a liquid discharging device.

9. The method for detecting a biochip according to claim 8, wherein the bracket is configured to support the liquid discharging needle.

10. The method for detecting a biochip according to claim 9, wherein a cover plate for fastening the test tube vial is further provided between the bracket and the cavity.

11. The method for detecting a biochip according to claim 8, wherein the liquid discharging needle is provided adjacent to the liquid separating needle, and the cap of the test tube vial is correspondingly provided with one liquid separating needle and one liquid discharging needle.

12. The method for detecting a biochip according to claim 6, wherein two ends of the cavity are each provided with a guide rail in a vertical direction, and two ends of the bracket are slidably connected to corresponding guide rails through guide blocks, respectively.

13. The method for detecting a biochip according to claim 1, wherein a heating and cooling sheet are provided at a bottom of the cavity, so as to realize temperature control of the cavity through cold and heat conduction.

14. The method for detecting a biochip according to claim 13, wherein a heat dissipation device is further provided below the heating and cooling sheet.

15. The method for detecting a biochip according to claim 1, wherein the liquid storage device comprises a plurality of liquid storage bottles, wherein the plurality of liquid storage bottles control mixing and outflow of different solutions through a liquid separating valve.

16. The method for detecting a biochip according to claim 1, wherein the biochip detection apparatus further comprises a platform, wherein the cavity, the liquid storage device, the pumping device, the bracket, and the imaging device are all mounted on the platform.

17. The method for detecting a biochip according to claim 16, wherein the cavity is mounted on one side of the platform, the bracket is mounted above the cavity, a mounting plate is vertically fixed on the other side of the platform close to the cavity, the plurality of liquid storage bottles of the liquid storage device are fixed on a side surface of the mounting plate facing away from the cavity, a pumping device is located between the cavity and the mounting plate, and the imaging device is mounted on one side of the cavity in parallel.

18. The method for detecting a biochip according to claim 1, wherein the imaging device is movably disposed.

19. The method for detecting a biochip according to claim 18, wherein a hollowed side of the cavity is provided with a rail along a direction parallel to the cavity, and the imaging device is slidably connected to the rail through a sliding block.

* * * * *